United States Patent [19]

Lau et al.

[11] Patent Number: 4,778,817
[45] Date of Patent: Oct. 18, 1988

[54] NAPHTHYL IMIDAZOLYL COMPOUNDS AND PHARMACEUTICAL COMPOSITIONS

[75] Inventors: Hans-Hermann Lau; Wilhelm Bartmann, both of Bad Soden am Taunus; Gerhard Beck, Frankfurt am Main; Günther Wess, Erlensee, all of Fed. Rep. of Germany

[73] Assignee: Hoechst Aktiengesellschaft, Fed. Rep. of Germany

[21] Appl. No.: 838,565

[22] Filed: Mar. 11, 1986

[30] Foreign Application Priority Data

Mar. 13, 1985 [DE] Fed. Rep. of Germany ....... 3508905

[51] Int. Cl.$^4$ .................. A61K 31/415; C07D 233/60
[52] U.S. Cl. ..................................... 514/399; 514/396; 514/397; 514/398; 546/278; 548/335; 548/336; 548/337; 548/341
[58] Field of Search ............... 548/337, 335, 336, 341; 514/396, 397, 398, 399; 546/278

[56] References Cited

U.S. PATENT DOCUMENTS 4,496,572  1/1985  Cross et al. .................. 548/335

FOREIGN PATENT DOCUMENTS 0003560  8/1979  European Pat. Off. .
0015002  9/1980  European Pat. Off. .
0073663  3/1983  European Pat. Off. .
0135177  3/1985  European Pat. Off. .

Primary Examiner—Robert W. Ramsuer
Attorney, Agent, or Firm—Finnegan, Henderson Farabow, Garrett and Dunner

[57] ABSTRACT

Compounds of the formula I

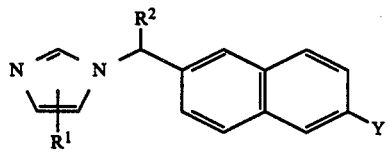

in which $R^1$, $R^2$ and Y have the indicated meanings, their physiologically tolerated acid addition salts, and a process for the preparation of these compounds are described. The compounds inhibit thromboxane synthetase and can thus be used as medicaments.

2 Claims, No Drawings

NAPHTHYL IMIDAZOLYL COMPOUNDS AND PHARMACEUTICAL COMPOSITIONS

Imidazole and its 1-substituted derivatives inhibit thromboxane synthetase (H.-H. Tai, Biochem. and Biophys. Res. Comm. 80, 236 (1978)).

The enzyme thromboxane synthetase catalyzes, within arachidonic acid metabolism, the conversion of prostaglandin endoperoxides ($PGH_2$ and $PGG_2$) into the highly biologically active thromboxane $A_2$ ($TXA_2$), which induces the aggregation of blood platelets and has a powerful constrictive action on smooth muscle. $TXA_2$ plays an essential part in hemostasis, in pathological situations with an increased tendency to vasospasms and/or thrombosis. In addition, $TXA_2$ has a powerful contracting effect on bronchial muscles in vitro and in vivo (B. Samuelson, Angew. Chem., 95, 854 (1983)).

The new 1-imidazolylalkylnaphthoic acids, their acid derivatives and 1-imidazolylalkylnaphthylmethanols, which are described in the present invention, are distinguished by a specific inhibitory effect on the enzyme thromboxane synthetase.

Thus the compounds are suitable for the prophylaxis or for the treatment of diseases with a deranged (increased) tendency to platelet aggregation, and where the thromboxane levels are pathologically increased, which are found in association with ischemia, angina pectoris, thromboembolic disorders, atherosclerosis, coronary spasms, arrhythmias, cerebral ischemic attacks, migraine and other vascular headaches, myocardial infarct, hypertension, breathing disturbances such as asthma and apnea, inflammatory diseases and microvascular complications associated with diabetes mellitus. The compounds according to the invention exert a favorable effect on disorders with increased thromboxane levels in various organs, for example in the region of the kidneys or in the gastrointestinal tract associated with colitis or with inflammatory bowel disease. Moreover, the compounds are suitable for slowing down or for preventing the proliferation of tumor cells. European Pat. No. A2-0073663 relates to, inter alia, 1-imidazolylalkylnaphthoic acid derivatives which have pharmacological activity.

The present invention relates to new 6-(1-imidazolylalkyl)-2-naphthoic acids, to their derivatives and to 6-(1-imidazolylalkyl)-2-naphthylmethanols of the general formula I

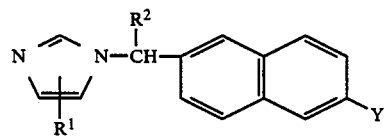

and to the physiologically tolerated acid addition salts.
In the general formula I,
$R^1$ denotes hydrogen, or, in the 2-, 4- or 5-position, a straight-chain or branched alkyl radical having up to 8 carbon atoms, a straight-chain or branched unsaturated hydrocarbon radical having up to 8 carbon atoms and 1-3 double or triple bonds, it being possible for the aliphatic radicals in turn to be substituted 1 to 3 times with halogen, with a carboxyl or carbalkoxy radical having up to 6 carbon atoms, alkoxy having up to 6 carbon atoms, cycloalkyl having 3–8 carbon atoms, or with a phenyl, α-or β-furyl or α- or β-thienyl radical, which in turn can be substituted 1 to 3 times in the nucleis by halogen, trifluoromethyl and/or alkyl or alkoxy having up to 6 carbon atoms, or denotes a straight-chain or branched alkoxy radical having up to 6 carbon atoms, or a phenyl radical which can be substituted 1-3 times in the nucleus by halogen, trifluoromethyl, alkyl or alkoxy having up to 6 carbon atoms, $R^2$ denotes hydrogen, a cycloaliphatic hydrocarbon radical having 3–8 carbon atoms, a straight-chain or branched alkyl radical having up to 8 carbon atoms, a straight-chain or branched unsaturated hydrocarbon radical having up to 8 carbon atoms and 1-3 double or triple bonds, it being possible for the aliphatic radicals in turn to be substituted 1-3 times with alkoxy having up to 6 carbon atoms, with cycloalkyl having 3–8 carbon atoms or with a phenyl radical which in turn can be substituted 1-3 times in the nucleus by halogen, trifluoromethyl, alkyl or alkoxy, each having up to 6 carbon atoms, or denotes a carboxyl or carbalkoxy radical having up to 6 carbon atoms, a phenyl radical which in turn can be substituted in the nucleus 1-3 times by halogen, trifluoromethyl, alkyl or alkoxy, each having up to 6 carbon atoms, or denotes a 2-, 3- or 4-pyridyl radical which can be substituted in the 4- or 5-position by alkyl having 1-4 carbon atoms, Y denotes a radical of the formula $-CO_2R^3$,

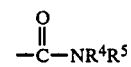

or $-CH_2OH$, $R^3$ denoting hydrogen, a straight-chain or branched alkyl radical having up to 8 carbon atoms, a straight-chain or branched unsaturated aliphatic hydrocarbon radical having up to 6 carbon atoms, a cycloaliphatic hydrocarbon radical having 3–7 carbon atoms, an araliphatic hydrocarbon radical having 7–10 carbon atoms, or a physiologically tolerated metal ion, $NH_4$ ion or an ammonium ion which is derived from a primary, secondary or tertiary amine, or a tetraalkylammonium ion, $R^4$ denoting hydrogen, a straight-chain or branched alkyl radical having up to 8 carbon atoms, a cycloaliphatic hydrocarbon radical having 3–7 carbon atoms, an araliphatic hydrocarbon radical having 7–10 carbon atoms which can be substituted in the nucleus 1–3 times by halogen, trifluoromethyl, alkyl and/or alkoxy, each having 1–6 carbon atoms, or a phenyl radical which can be substituted in the nucleus 1-3 times by halogen, trifluoromethyl, alkyl and/or alkoxy, each having 1-6 carbon atoms, $R^5$ denoting hydrogen, a straight-chain or branched alkyl radical having up to 8 carbon atoms, or a cycloaliphatic hydrocarbon radical having 3–7 carbon atoms, or $R^4$ and $R^5$ together denoting a $-(CH_2)_p-$ group with p=3–6, or a $-(CH_2)_q-Z-(CH_2)_q-$ group with q=2 or 3 and Z=oxygen or an $N-R^6$ group, $R^6$ denoting hydrogen or a straight-chain or branched alkyl radical having 1-6 carbon atoms, with the exception of the compounds of the formula I in which $R^1$ and $R^2$ are both hydrogen if Y represents the group $CO_2R^3$, with $R^3$ representing H or alkyl, or represents the group $CONH_2$.

The following substituents $R^1$ are preferred: Hydrogen, or, in the 5-position, straight-chain or branched alkyl having up to 6 carbon atoms, in particular $C_1$–$C_4$-alkyl, a straight-chain or branched unsaturated aliphatic hydrocarbon radical having up to 4 carbon atoms, in particular $C_2$–$C_4$-alkenyl, phenyl-$C_1$–$C_3$-alkyl, in particular benzyl or 2-phenylethyl, a carboxyalkyl radical having 2 to 4 carbon atoms, in particular carboxymethyl or carboxyethyl, or an alkoxycarbonylalkyl radical having up to 7 carbon atoms, in particular ethoxycarbonylmethyl or methoxycarbonylmethyl or ethoxycarbonylethyl or methoxycarbonylethyl, or phenyl.

The following substituents $R^2$ are particularly preferred: Hydrogen, straight-chain or branched alkyl having up to 6 carbon atoms, in particular $C_1$–$C_4$-alkyl, a cycloaliphatic hydrocarbon radical having 5–7 carbon atoms, in particular $C_5$–$C_7$-cycloalkyl, phenyl-$C_1$–$C_3$-alkyl, in particular benzyl or 2-phenylethyl, phenyl whose nucleus is preferably unsubstituted or is substituted 1–2 times by $C_1$–$C_3$-alkyl, in particular methyl or ethyl, by $C_1$–$C_3$-alkoxy, in particular methoxy or ethoxy, by halogen or by trifluoromethyl, or 3-pyridyl which can be substituted in the 4- or 5-position by $C_1$–$C_4$-alkyl, in particular by methyl or ethyl.

The preferred meaning of Y is —$CO_2R^3$, $$-\overset{\overset{O}{\|}}{C}-NR^4R^5$$

or $CH_2$—OH, the following meanings of $R^3$, $R^4$ and $R^5$ being suitable and preferred:

$R^3$: hydrogen, straight-chain or branched alkyl having 1–6 carbon atoms, in particular $C_1$–$C_4$-alkyl, a straight-chain or branched unsaturated aliphatic hydrocarbon radical having up to 4 carbon atoms, in particular $C_2$–$C_4$-alkenyl, a cycloaliphatic hydrocarbon radical having 5–7 carbon atoms, in particular $C_5$–$C_7$-cycloalkyl, phenyl-$C_1$–$C_3$-alkyl, in particular phenethyl or benzyl, or a physiologically tolerated metal ion, $NH_4$ ion or an ammonium ion which is derived from a primary, secondary or tertiary amine, in particular:

Hydrogen, methyl, ethyl, n-butyl, n-pentyl, n-hexyl, n-heptyl, 2-propyl, 2-butyl, 2-pentyl, 3-hexyl, 2-methylpropyl, 2-methylbutyl, 4,4-dimethylpentyl, 5,5-dimethylhexyl, cyclopentyl, cyclohexyl, cycloheptyl, methylammonium, dicyclohexylammonium or tris(hydroxymethyl)methylammonium.

$R^4$: hydrogen, straight-chain or branched alkyl having up to 6 carbon atoms, in particular $C_1$–$C_4$-alkyl, $C_5$–$C_7$-cycloalkyl, in particular cyclopentyl and cyclohexyl, phenyl-$C_1$–$C_3$-alkyl, in particular benzyl and 2-phenylethyl, or a phenyl radical.

$R^5$: hydrogen, straight-chain or branched alkyl having up to 6 carbon atoms, in particular $C_1$–$C_4$-alkyl.

$R^4$ and $R^5$ can, together, preferably mean: a —$(CH_2)_p$— group with p=4 or 5, or a —$(CH_2)_2$—O—$(CH_2)_2$— group.

Very particular importance attaches to compounds of the formula I in which $R^1$ represents hydrogen or $C_1$–$C_4$-alkyl or phenyl, each in the 5-position, $R^2$ represents hydrogen or $C_1$–$C_2$-alkyl, and Y represents the COOH or COO—$R^3$ group, $R^3$ denoting $C_1$–$C_4$-alkyl, and the physiologically tolerated acid addition salts.

The invention also relates to the acid addition salts of the compounds which have been described with inorganic or organic acids, for example hydrochloric acid, hydrobromic acid, sulfuric acid, phosphoric acid, nitric acid, acetic acid, propionic acid, oxalic acid, malonic acid, glycollic acid, succinic acid, maleic acid, fumaric acid, tartaric acid, citric acid, benzoic acid or cinnamic acid.

The invention also relates to a process for the preparation of compounds of the formula I, which comprises
(a) reaction of a compound of the formula II

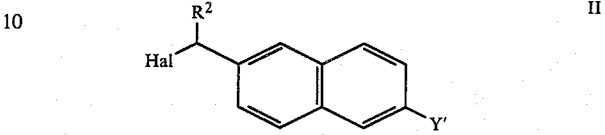

in which
$R^2$ has the meaning indicated for formula I,
Y' denotes the radicals

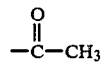

or —$COOR^7$, $R^7$ representing $C_1$–$C_8$-alkyl, and Hal denotes chlorine or bromine,
with an imidazole of the formula III

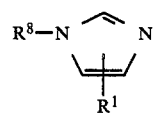

in which
$R^1$ has the meaning indicated for formula I, and
$R^8$ denotes hydrogen, lower alkanoyl or benzoyl, to give a compound of the formula IV

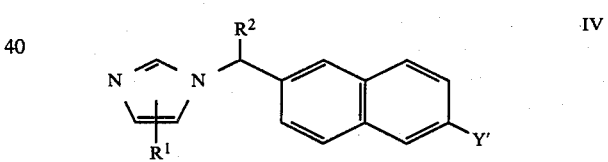

in which
$R^1$ and $R^2$ have the meanings indicated for formula I, and
Y' has the meanings indicated for formula II,
(b) optionally, oxidation of a compound of the formula IV, in which
Y' represents the radical

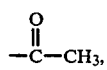

to give a compound of the formula I, in which Y denotes the radical —COOH,
(c) optionally, hydrolysis of a compound of the formula I, in which Y represents the radical —$COOR^3$, $R^3$ having the meanings indicated for formula I, but not representing hydrogen or a cation, to give a compound of the formula I, in which Y represents the radical —COOH,
(d) optionally, conversion of a compound of the formula I, in which Y represents the radical —COOH, into the corresponding esters or salts of the formula I, in which Y denotes the radical —COOR$^3$ with R$^3\neq$hydrogen, or into the corresponding amides of the formula I, in which Y represents the radical

R$^4$ and R$^5$ having the meanings indicated for formula I, or (e) optionally, reduction of a compound of the formula I, in which Y represents the radical —COOR$^3$, to a compound of the formula I, in which Y represents the radical —CH$_2$OH, and (f) optionally, conversion of a resulting compound of the formula I into the acid addition salts.

It is possible to carry out one or more of the optional measures; the sequence of the measures (c) and (d) is arbitrary.

The starting compounds of the formula II are either known or can be obtained by methods described in the literature. Thus, they are obtained by, for example, halogenation of a compound of the formula V

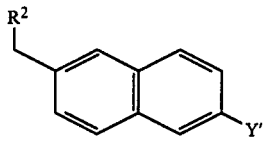

in which
R$^2$ has the meanings indicated for formula I and
Y' has the meanings indicated for formula II.

2-Acetylnapthalene derivatives of the general formula V can be prepared by known processes (for example J. Org. Chem., 49, 384 (1984) or Eur. J. Med. Chem.-Chim. Ther., 19, 5 (1984)).

Compounds of the formula II with Y'=CO$_2$R$^7$ can be obtained, inter alia, by the process described in German Offenlegungsschrift No. 2,363,416.

Imidazole derivatives of the formula III with R$^8$=acyl can be prepared by processes known from the literature (for example J. Amer. Chem. Soc., 74, 6274 (1952) or J. Org. Chem., 45, 4038 (1980)).

Compounds of the formula I with Y=CO$_2$R$^3$, in which R$^3$ denotes alkyl, and compounds of the formula IV, are advantageously obtained by reaction of imidazole derivatives of the formula III, with R$^8$=hydrogen, with compounds of the formula II in the presence of suitable strong bases such as, for example, sodium hydride, sodium hydroxide, sodium alcoholate, potassium t-butylate or potassium carbonate in an inert solvent, such as ether, tetrahydrofuran, dimethoxyethane, dioxane, toluene, xylene, acetone, formamides, dimethyl sulfoxide or alcohols, between 0° and 180° C.

Compounds of the formula I with Y=CO$_2$R$^3$ with R$^3$=alkyl, or compounds of the formula IV, are likewise obtained when imidazole derivatives of the formula III, with R$^8$=acyl, are reacted with compounds of the formula II in a suitable solvent, in particular acetonitrile, at temperatures between 0° and 80° C. (see Chem. Pharm. Bull., 30, 4242 (1982)).

The imidazolyl ketones of the formula IV can be oxidized in a haloform reaction with chlorine, bromine or iodine, in the presence of a strong base such as, for example, sodium or potassium hydroxide, to give compounds of the formula I, in which Y denotes a carboxyl group.

It is possible by processes known from the literature to prepare from compounds of the formula I with Y=carboxyl the corresponding esters, amides and salts.

The reduction of the ester or acid group in compounds of the formula I to give compounds of the formula I with Y=CH$_2$—OH is accomplished with, inter alia, complex metal hydrides, such as lithium alanate or sodium boronate, in a suitable inert solvent.

Where the individual reaction products are not obtained in a form which is already sufficiently pure for it to be possible to use them in the subsequent reaction step, purification by crystallization or column, thin-layer or high-pressure liquid chromatography is advisable.

The compounds of the general formula I exhibit a specific inhibition of thromboxane synthetase and can thus be used as medicaments for the prophylaxis or treatment of diseases with a deranged, i.e. increased, tendency of the platelets to aggregate, as well as when the thromboxane levels are pathologically increased, such as is found in association with ischemia, angina pectoris, thromboembolic disorders, atherosclerosis, coronary spasms, arrhythmias, cerebral ischemic attacks, migraine and other vascular headaches, myocardial infarct, hypertension, breathing disturbances such as asthma or apnea, inflammatory disorders and microvascular complications associated with diabetes mellitus. The compounds according to the invention exert a favorable effect on disorders with increased thromboxane levels in various organs, for example in the region of the kidneys or the stomach and intestines associated with colitis or inflammatory bowel disease. The compounds are, moreover, suitable for slowing down, or even preventing, the proliferation of tumor cells.

The metabolites of arachidonic acid are involved in a number of physiological and pathophysiological processes. Prostacyclin (PGI$_2$) and thromboxane A$_2$ (TXA$_2$) are of essential importance in the regulation of the tone of blood vessels and of platelet aggregation. Prostacyclin, which is formed from prostaglandin endoperoxide H$_2$ (PGH$_2$) preferentially in the endothelial cells of the blood vessels, brings about vasodilatation and simultaneously prevents the aggregation of platelets. The conversion of PGH$_2$ into prostacyclin is catalyzed by prostacyclin synthetase. The physiological antagonist of prostacyclin is thromboxane A$_2$, which is synthesized from PGH$_2$ mainly in the blood platelets. This reaction is catalyzed by the enzyme thromboxane synthetase. TXA$_2$ brings about aggregation of blood platelets and results in vasoconstriction. It is the most potent vasoconstrictor hitherto known in the human body (see A. G. Herman, P. M. Vonhoutte, H. Denolin, A. Goossens, Cardiovascular Pharmacology of the Prostaglandins, Raven Press, New York, 1982). Disturbances of the equilibrium between prostacyclin and thromboxane A$_2$ result in pathophysiological situations. Thus, when the PGI$_2$ levels remain the same, an increase in the thromboxane level results in aggregation of blood platelets and in vasospasms as well as in an increased susceptibility to atherothrombosis Lancet 1977, 479; Science 1976, 1135; Amer. J. Cardiology 41, 787 (1978); Lancet 1977, 1216). In experimental atherosclerosis, the formation of PGI$_2$ is inhibited with, at the same time, an increase in the formation of thromboxane A$_2$ (Prostaglandins 14, 1025 and 1035 (1977)). For this reason, TXA$_2$ is thought to be connected with various types of angina, the development of myocardial infarcts, sudden heart death and strokes (Thromb. Haemostasis 38, 132 (1977); Platelets, Prostaglandins and Cardiovascular System, Florence, February 1984).

Another area in which a disturbance of the $PGI_2/TXA_2$ equilibrium is regarded as being a contributory factor is migraine. Migrainous headaches are linked with changes in the intracerebral and extracerebral blood flow, in particular with a reduction in the cerebral blood flow taking place before the manifestation of the headache and with subsequent dilatation in both vascular areas during the headache phase. Platelets from migraine patients have a greater tendency to aggregate than do those from normal individuals (J. clin. Pathol. 24, 250 (1971); J. Headache, 17, 101 (1977); Lancet 1978, 501).

In patients with diabetes mellitus, an imbalance between prostacyclin and thromboxane $A_2$ is regarded as being the cause of the microvascular complications. Platelets from diabetes patients form increased amounts of $TXA_2$ and malondialdehyde (Symposium "Diabetes and Thrombosis Implications for Therapy", Leeds, Great Britain, April 1979). It has also been shown that, in rats with experimentally induced diabetes, the vascular $PGI_2$ formation is inhibited whereas the $TXA_2$ synthesis in the platelets is increased (IV. Int. Prostaglandin Conference, Washington DC, May 1979).

Non-steroidal antiinflammatory agents inhibit cyclooxygenase, which catalyses the conversion of arachidonic acid into $PGH_2$ via $PGG_2$. Thus they intervene both in the biosynthesis of thromboxane $A_2$ and in that of prostacyclin. Thus, more valuable compounds would be those which specifically block the formation of thromboxane $A_2$ by inhibition of thromboxane synthetase and, at the same time, have no effect on the formation of prostacyclin.

REPORT OF EXPERIMENTS

The Biochemical and Pharmacological Activities were Determined in the Following Test Systems 1. Inhibition of the arachidonic acid-induced aggregation of human platelets in vitro.

Blood is taken, by careful cannulation of the antecubital vein, from apparently healthy male and female volunteers, who have taken no medicaments in the preceding 10-day period, and is immediately stabilized with sodium citrate (ad. 0.38%). Platelet-rich plasma (PRP) is obtained in the supernatant by centrifugation at $140 \times g$ for 15 minutes, and the platelet content of this should be in the range $2.5-3.5 \times 10^8$/ml (Coulter counter). The platelet aggregation is followed optically by measurement of the transmission of light in a Born aggregometer. The total volume of the test mix is 0.25 ml. The preincubation time at 37° C. with the test product is 10 min, and aggregation is then induced with $2 \times 10^{-4}$M arachidonic acid. The test product is, as a rule, tested in five different concentrations in the PRP from three different donors. Dose-effect curves are drawn from the maximal aggregation amplitudes in each case, and the $IC_{50}$ values* are determined graphically. The measurements are carried out in the period 1-6 hours after blood sampling.

*($IC_{50}$ is the concentration which brings about 50% inhibition of the arachidonic acid-induced aggregation).

The following $IC_{50}$ values for the inhibition of the arachidonic acid-induced aggregation of human platelets in vitro were determined by the method described above for the compounds according to the invention:

| Example | $IC_{50}$ value (mol/l) |
|---|---|
| 2 | $3 \times 10^{-6}$ |
| 4 | $5.4 \times 10^{-7}$ |

2. Thrombin-induced $TXA_2$ release in platelet-rich human plasma in vitro

Blood is taken, by careful cannulation of the antecubital vein, from apparently healthy male and female volunteers, who have taken no medicaments in the preceding 10-day period, and is immediately stabilized with sodium citrate (ad. 0.38%). Platelet-rich plasma (PRP) is obtained in the supernatant by centrifugation at $140 \times g$ for 15 minutes, and the platelet content of this should be in the range $2.5-3.5 \times 10^8$/ml. The platelets are sedimented by renewed centrifugation (10 min at $2,000 \times g$), and then resolubilized in Tyrode's solution (about $7 \times 10^7$ platelets/ml, total volume per measurement 0.5 ml). After addition of test substance, the mixture is incubated at 37° C. for 10 min, and then $7.2 \times 10^{-7}$M arachidonic acid and 0.5 U thrombin are added, and incubation is carried out at 37° C. for 30 min. This is stopped in an ice bath and, after addition of tracer and $TXB_2$-specific antibodies (NEN, Dreieich), the $TXB_2$ content is determined radioimmunologically ($TXA_2$ is unstable under the experimental conditions and thus cannot be measured. The stable hydrolysis product $TXB_2$ is measured in its place). The measured variable is the relative $TXB_2$ content in the platelet incubations from two or three different donors with and without (=100%) the test substance.

The following figures for the $TXB_2$ release after administration of the test substance were determined, for example, for the compounds according to the invention by the method described above:

| Example | $TXB_2$ release |
|---|---|
| 2 | $10^{-6}$ mol/l: 31% |
|   | $10^{-7}$ mol/l: 55% |
| 4 | $10^{-6}$ mol/l: 9% |
|   | $10^{-7}$ mol/l: 19% |
|   | $10^{-8}$ mol/l: 98% |

3. Inhibition of laser-induced thrombosis

The investigations of the compounds according to the invention in the model of laser-induced thrombosis are carried out on male or female Sprague-Dawley rats with a body weight of about 200 g. The animals to be investigated are premedicated s.c. with 0.1 mg of atropine sulfate in solution, and anesthetized i.p. with 100 mg of ketamine hydrochloride and 4 mg of xylazine per kg of body weight. Arterioles from the mesentery, with a diameter of 12–25 $\mu$m, are used for the investigation. During the measurement, the exposed mesentery is hyperfused with warmed physiological NaCl (37° C.) or is covered with degassed liquid paraffin. The beam of a 4 W argon laser (supplied by Spectra Physics, Darmstadt, FRG) is introduced coaxially into the inverted ray path of a microscope (ICM 405, LD-Epilan 40/0.60; supplied by Zeiss, Oberkochen, FRG) by means of a ray adaptation and adjustment system (supplied by BTG, Munich, FRG). The wavelength used is 514.5 nm, with an energy above the objective of 40 mW. The single-shot exposure time is 1/15 sec. The diameter of the effective laser beam on the vessel is 10 $\mu$m, and with repeated exposure the next shot takes place 5 $\mu$m upstream in each case, directly on the vessel wall. All the measurement procedures are filmed by video camera (Sony, Trinicon tube) and stored in a recorder (Sony, U-matic ¾). A survey image of the terminal vessels which are to be investigated is provided by the transillumination method using the same microscope with low magnification (LD-Epilan 8/0.20). A video-analyzer and a correlator are used to determine the rate of flow in the arterioles under investigation.

The test substances were administered orally in various doses in 0.9% sodium chloride solution (contained 1% carboxymethylcellulose, or in appropriate solubilizers) to the experimental animals one hour before the start of the experiment; control animals were treated in a corresponding manner, but without the test substances. The investigations were carried out with randomization as a double-blind study.

Evaluation:

The number of shots needed to induce a defined thrombus was counted. The frequency of the laser flashes was one lesion every 2 minutes, all the thrombi with a minimum size of ¼ of the vessel radius which were formed during the observation period being counted and measured. The results of the experiment were statistically analyzed using the $X^2$ test (L. Cavalli-Sforza, Biometrie, Stuttgart, 1969, page 49 et seq.).

| Example | Number of laser shots to form a thrombus (compared with control) | |
| --- | --- | --- |
| 4 | 10 mg/kg p.o. | +96% |
|  | 5 mg/kg p.o. | +53% |
|  | 1 mg/kg p.o. | +16% |

The compounds of the formula I specifically block the formation of thromboxane $A_2$ by inhibition of thromboxane synthetase, without affecting prostacyclin formation, and are thus suitable for the prevention or for the treatment of the abovementioned disorders which respond to inhibition of thromboxane synthetase.

The invention thus also relates to the use of the compounds of the formula I, and of their salts, for the treatment of the abovementioned disorders, and to pharmaceutical products based on the compounds according to the invention. The compounds of the formula I are administered in various dosage forms, for example orally in the form of tablets, capsules or liquids, rectally in the form of suppositories, parenterally, subcutaneously or intramuscularly, preference being given to intravenous administration in emergency situations.

The compounds of the formula I, according to the invention, can be used as free bases or in the form of their physiologically acceptable inorganic or organic acid addition salts. The free bases and acid addition salts can be used in the form of their aqueous solutions or suspensions, or dissolved or suspended in pharmacologically acceptable organic solvents, such as monohydric or polyhydric alcohols such as, for example, ethanol, ethylene glycol or glycerol, in triacetin, in alcohol-/acetaldehyde diacetal mixtures, oils such as, for example, sunflower oil or fish liver oil, ethers such as, for example, diethylene glycol dimethyl ether, or polyethers such as, for example, polyethylene glycol, or in the presence of other pharmacologically acceptable polymeric vehicles such as, for example, polyvinylpyrrolidone.

Suitable formulations are the customary pharmaceutical solutions for infusion or injection, and tablets, as well as formulations which can be used locally, such as creams, emulsions, suppositories or aerosols.

The compounds are active in doses from 0.01 mg/kg to 10 mg/kg. The single dose administered can be between 1 mg and 500 mg. The preferred daily dose on oral administration is between 1 mg and 1 g.

EXAMPLE 1

Methyl 6-(5-methyl-1-imidazolylmethyl)-2-naphthoate (α) 1-Acetyl-4-methylimidazole 50 g (0.6 mol) of 4-methylimidazole are dissolved in 500 ml of absolute ether. After dropwise addition of 23.6 g (0.3 mol) of acetyl chloride in 75 ml of absolute ether at room temperature, the mixture is heated under reflux for 11 hours. The residue is removed by filtration, and the solution is evaporated in vacuo. 11.45 g (31%) of 1-acetyl-4-methylimidazole are obtained as a colorless oil.

$^1$H-NMR (CDCl$_3$, 60 MHz) δ=2.15 and 2.5 (2s, 6H; 2×CH$_3$), 7.05 (s, 1H; C-5-H), 7.95 (s, 1H; C-2-H).

(β) Methyl 6-(5-methyl-1-imidazolylmethyl)-2-naphthoate 2 g (7.16 mmol) of methyl 6-bromomethyl-2-naphthoate and 1.07 g (8.6 mmol) of 1-acetyl-4-methylimidazole are heated under reflux in absolute acetonitrile (8 hours). After the reaction solution has been evaporated, the residue is taken up in 2N HCl, and the solution is extracted with ethyl acetate. The ethyl acetate phases are discarded. After the aqueous phase has been neutralized with sodium carbonate, it is extracted with ethyl acetate, and the ethyl acetate phase is dried and evaporated in vacuo. 1.4 g (70%) of methyl 6-(5-methyl-1-imidazolylmethyl)-2-naphthoate are obtained by trituration of the residue with ether. Melting point 101°–102° C.

$^1$H-NMR (CDCl$_3$, 60 MHz) δ=2.1 (d, J=1.5 Hz, 3H; C—CH$_3$), 3.95 (s, 3H; OCH$_3$), 5.2 (s, 2H; CH$_2$), 6.85–8.55 (m, 8H; arom. H).

EXAMPLE 2

6-[1-(1-Imidazolyl)ethyl]-2-naphthoic acid hydrochloride (α) 2-Acetyl-6-ethylnaphthalene 100 g (0.75 mol) of aluminum chloride are dissolved in 200 ml of distilled nitrobenzene. At 70° C., a solution of 100 g (0.64 mol) of 2-ethylnaphthalene and 52 ml (57.4 g, 0.73 mol) of acetyl chloride in 400 ml of distilled nitrobenzene is added dropwise, and the mixture is then stirred for 4 hours. The reaction mixture is poured onto ice and acidified with 300 ml of 2N HCl, filtered through a clarification layer and the phases are separated. The organic phase is washed with 2N HCl, sodium carbonate solution and, finally, with water; the aqueous phases are reextracted with dichloromethane. The organic phases are dried and then distilled in vacuo. 80.3 g (63%) of a 5:2 mixture of 2-acetyl-6-ethylnaphthalene and 1-acetyl-7-ethylnaphthalene are obtained. Boiling point (0.2):125° C..

To separate the isomers, the mixture is heated with 44.3 ml (49.6 g, 0.8 mol) of ethylene glycol and 0.5 g of p-toluenesulfonic acid in 800 ml of toluene under reflux with a water separator until no more water separates out and are thus converted into the isomeric ethylene acetals. The reaction solution is washed with sodium bicarbonate solution and then evaporated in vacuo. 97.4 g (102%) of a mixture of two isomeric ethylene acetals are obtained, 40 g of which is separated into the isomers by chromatography on silica gel using cyclohexane/ethyl acetate mixtures. 11.5 g (47.5 mmol) of 7-ethyl-1-naphthyl methyl ketone ethylene acetal are obtained as an oil, RF (cyclohexane/ethyl acetate 7:1): 0.38, and 25.5 g of an oil from which 16.1 g (31%) of 6-ethyl-2-naphthyl methyl ketone ethylene acetal can be isolated by recrystallization from petroleum ether are obtained. Melting point 66°–68° C., RF (cyclohexane/ethyl acetate 7:1): 0.30.

Then 16.1 g (66.4 mmol) of 6-ethyl-2-naphthyl methyl ketone ethylene acetal are dissolved in 100 ml of tetrahydrofuran, and 100 ml of methanol and 100 ml of 2N HCl are added, and the mixture is heated under reflux for 3 hours. After the solution has been evaporated to one-half of the volume, it is neutralized with saturated sodium bicarbonate solution and extracted with ethyl acetate. The ethyl acetate phase is dried and evaporated in vacuo. 12.9 g (98%) of 2-acetyl-6-ethylnaphthalene are obtained as an oil. RF (cyclohexane/ethyl acetate 7:1): 0.19.

$^1$H—NMR (CDCl$_3$, 60 MHz) $\delta$=1.3 (t, 3H; CH$_2$—CH$_3$), 2.65 (s, 3H; CH$_3$—CO), 2.8 (q, 2H; CH$_2$), 7.1–8.0 (m, 5H; arom. H), 8.3 (s, 1H; C—1—H).

($\beta$) 2-Acetyl-6-(1-bromoethyl)naphthalene 12.8 g (64.6 mmol) of 2-acetyl-6-ethylnaphthalene, 10.92 g (61.35 mmol) of N-bromosuccinimide and 0.1 g of azobisisobutyronitrile in 280 ml of absolute tetrachloromethane are heated under reflux for one hour. The residue is removed by filtration, washed with hot tetrachloromethane, and the tetrachloromethane solution is evaporated in vacuo. 9.84 g (58%) of 2-acetyl-6-(1-bromoethyl)naphthalene are obtained by recrystallization of the residue from n-hexane/ethyl acetate. Melting point 64°–66° C.

$^1$H—NMR (CDCl$_3$, 60 MHz) $\delta$=2.1 (d, 3H; CH—CH$_3$), 2.7 (s, 3H; C(O)—CH$_3$), 5.3 (q, 1H; CH), 7.4–8.1 (m, 5H; arom. H), 8.3 (s, 1H; C—1—H).

($\gamma$) 2-Acetyl-6-[1-(1-imidazolyl)ethyl]naphthalene 9.82 g (35.4 mmol) of 2-acetyl-6-(1-bromoethyl)naphthalene, 6.38 g (70.9 mmol) of sodium imidazolide (from 3.1 g (70.9 mmol) of sodium hydride dispersion (55%) and 4.83 g (70.9 mmol) of imidazole) and 0.588 g (3.54 mmol) of potassium iodide in 100 ml of absolute N,N-dimethylformamide are stirred at 100° C. (24 hours). The mixture is then evaporated in vacuo, the residue is taken up in 4N HCl, the solution is extracted with ethyl acetate, and the aqueous phase is neutralized with sodium carbonate solution. It is then extracted 4× with dichloromethane, and the dichloromethane phase is dried and evaporated in vacuo. The residue is filtered through silica gel using ethyl acetate/methanol 8:1. 6.48 g (70%) of 2-acetyl-6-[1-(1-imidazolyl)ethyl]naphthalene are obtained as an oil. R$_F$ (ethyl acetate/methanol 8:1): 0.15.

$^1$H—NMR (CDCl$_3$, 60 MHz) $\delta$=1.95 (d, 3H, J=7 Hz; CH$_3$), 2.7 (s, 3H; CH$_3$), 5.5 (q, 1H; CH), 6.9–8.1 (m, 8H; arom. H), 8.4 (s, 1H; C—1—H).

($\delta$) 6-[1-(1-Imidazolyl)ethyl]-2-naphthoic acid hydrochloride 9.72 g (0.243 mol) of sodium hydroxide are dissolved in 50 ml of water and, at 0° to 10° C., 3.75 ml (11.65 g, 72.9 mmol) of bromine are added. At 0° to 10° C., a solution of 6.4 g (24.3 mmol) of 2-acetyl-6-[1-(imidazolyl) ethyl]naphthalene in 15 ml of dioxane is added dropwise. The mixture is stirred at room temperature for 3 hours. After addition of 40 ml of saturated sodium bisulfite solution, the mixture is stirred for 30 minutes. It is extracted with ether, and the aqueous phase is then adjusted to pH 1 with 2N HCl, and is evaporated in vacuo. The residue is extracted by boiling with isopropanol. After recrystallization from 2N HCl, 3.12 g (43%) of 6-[1-(1-imidazolyl)ethyl]-2-naphthoic acid hydrochloride are obtained. Melting point 246°–249° C. (decomposition).

$^1$H—NMR (D$_2$O, 60 MHz) $\delta$=2.0 (d, 3H; CH$_3$), 6.0 (q, 1H; CH$_3$) 7.1–8.8 (m, 9H; arom. H).

EXAMPLE 3

6-(1-Imidazolylmethyl)-2-naphthylmethanol ($\alpha$) Methyl 6-(1-imidazolylmethyl)-2-naphthoate 10 g (35.8 mmol) of methyl 6-bromomethyl-2-naphthoate and 9.75 g (0.143 mol) of imidazole in 300 ml of dimethoxyethane are heated under reflux for 3 hours. After the reaction solution has been evaporated, the residue is taken up in 2N HCl, and the solution is extracted with ethyl acetate, and the ethyl acetate phase is discarded.

The aqueous phase is adjusted to pH 7 with sodium bicarbonate, and the precipitate is filtered off with suction. The residue is recrystallized from ethyl acetate with the addition of a little active charcoal. 7.16 g (75%) of methyl 6-(1-imidazolylmethyl)-2-naphthoate are obtained. Melting point 144°–146° C.

IR (KBr) 1710 cm$^{-1}$.

$^1$H—NMR (CDCl$_3$, 60 MHz) $\delta$=4.0 (s, 3H; CH$_3$), 5.3 (s, 2H; CH$_2$), 6.9–8.2 (m, 8H; arom. H), 8.55 (s, 1H; C—1—H).

($\delta$) 6-(1-Imidazolylmethyl)-2-naphthylmethanol 0.2 g (0.75 mmol) of methyl 6-(1-imidazolylmethyl)-2-naphthoate in 5 ml of absolute tetrahydrofuran are added dropwise to 28.5 mg (0.75 mmol) of lithium alanate in 1 ml of absolute tetrahydrofuran. The mixture is allowed to stand at room temperature overnight. Excess lithium alanate is destroyed by addition of 2N HCl. After neutralization with sodium bicarbonate, the mixture is extracted with ethyl acetate, and the ethyl acetate phase is dried and evaporated in vacuo. 0.13 g (73%) of 6-(1-imidazolylmethyl)-2-naphthylmethanol is obtained. Melting point 122°–125° C.

$^1$H—NMR (CDCl$_3$, 60 MHz) $\delta$=3.1 (b, 1H; OH) 4.8 (s, 2H; CH$_2$—O), 5.2 (s, 2H; CH$_2$—N), 6.8–7.9 (m, 9H; arom. H).

EXAMPLE 4

6-(5-Methyl-1-imidazolyl)methyl-2-naphthoic acid hydrochloride 3.31 g (11.8 mmol) of methyl 6-(5-methyl-1-imidazolyl)methyl-2-naphthoate in 40 ml of 2N HCl are heated under reflux for three hours, and active charcoal is added and the mixture is filtered hot. The hydrochloride of the acid crystallizes out on cooling. 3.03 g (85%) of 6-(5-methyl-1-imidazolyl)methyl-2-naphthoic acid hydrochloride are obtained after filtration with suction, washing with acetone and drying. Melting point: 289°–290° C.

$^1$H—NMR (D$_2$O, 60 MHz) $\delta$=2.15 (s, 3H; CH$_3$), 5.45 (s, 2H; CH$_2$), 7.1–8.7 (m, 8H; arom. H).

EXAMPLE 5

Methyl 6-[1-(1-imidazolyl)ethyl]-2-naphthoate 1.26 g (4.2 mmol) of 6-[1-(1-imidazolyl)ethyl]-2-naphthoic acid hydrochloride in 25 ml of saturated methanolic HCl solution are heated under reflux for one hour and then evaporated in vacuo. The residue is taken up in saturated sodium bicarbonate solution, and the solution is extracted with ethyl acetate. After the ethyl acetate solution has been dried and evaporated, the residue is chromatographed through silica gel (ethyl acetate/methanol 8:1). 530 mg (45%) of methyl 6-[1-(1-imidazolyl)ethyl]-2-naphthoate are obtained. Melting point 103°–106° C.

$^1$H—NMR (CDCl$_3$, 60 MHz) δ=1.95 (d, 3H; CH$_3$), 3.95 (s, 3H; OCH$_3$), 5.5 (q, 1H; CH), 6.9–8.6 (m, 9H; arom. H).

We claim:

1. A compond of the formula I

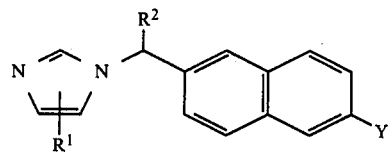

in which
R$^1$ is hydrogen or methyl in the 2-, 4- or 5- position;
R$^2$ is hydrogen or methyl; and
Y is a radical of the formula —CO$_2$R$^3$,
R$^3$ being hydrogen or alkyl having 1 to 4 carbon atoms, or a physiologically tolerated acid addition salt thereof, with the exception of the compounds of the formula I in which R$^1$ and R$^2$ are both hydrogen.

2. A medicament which contains a compound as claimed in claim 1 together with pharmaceutically customary auxiliaries and vehicles.

* * * * *